United States Patent [19]
Emery et al.

[11] Patent Number: 5,420,253
[45] Date of Patent: May 30, 1995

[54] METHOD FOR PURIFYING EGG YOLK IMMUNOGLOBULINS

[75] Inventors: Daryll A. Emery; Darren E. Straub, both of Willmar, Minn.

[73] Assignee: Willmar Poultry Company, Inc., Willmar, Minn.

[21] Appl. No.: 118,514

[22] Filed: Sep. 9, 1993

[51] Int. Cl.$^6$ .......................... A23J 1/08; C07K 1/30; C07K 16/02
[52] U.S. Cl. .................................. 530/423; 530/853; 530/861; 424/157.1
[58] Field of Search ....................... 530/422, 853, 861; 424/157.1

[56] References Cited

U.S. PATENT DOCUMENTS

| | | | |
|---|---|---|---|
| 4,550,019 | 10/1985 | Polson et al. | 424/157.1 |
| 4,855,090 | 8/1989 | Wallach | 264/4.1 |
| 5,100,662 | 3/1991 | Bolcsak et al. | 424/450 |
| 5,136,979 | 8/1992 | Paul et al. | 119/6.8 |

OTHER PUBLICATIONS

England et al. "Precipitation Techniques" in *Guide to Protein Purification*, Deutscher et al ed. Academic Press, Inc. San Diego. (Methods in Enzymology 182: 285–300, 1990).

Neugebauer, J. M., "Detergents: An Overview" in *Guide to Protein Purification* Deutscher et al. Academic Press, Inc. San Diego (Methods in Enzymology 182: 239–253, 1990).

Helenius et al, Biochimica et Biophysica Acta 415: 29–79, 1975.

Hjelmeland L. M., "Solubilization of Membrane Proteins" in *Guide to Protein Purification*, Deutscher et al ed. Academic Press, San Diego. (Methods in Enzymology 182: 253–264, 1990).

"Appendix B: Preparation of Reagents and Buffers Used in Molecular Cloning", B.1.

Bade et al., "Rapid Method of Extraction of Antibodies from Hen Egg Yolk", *J. of Immuno. Methods*, 72, 421–426 (1984).

Bollag et al., "Polyethylene Glycol (PEG) Precipitation", *Protein Methods*, Wiley-Liss, 84.

Bordier, "Phase Separation of Integral Membrane Proteins in Triton X-114 Solution", *J. Biol. Chem.*, 256, 1604–1607 (1981).

Cams et al., "Surfactants and Detersive Systems", *Kirk Othmer (Concise Encyclopedia of Chemical Technology)*, 1142–1146 (1985).

Goding, *Monoclonal Antibodies: Principles and Practice*, 2d ed., Academic Press, 161–164 (1986).

Goudswaard et al., "The Immunoglobulins of the Turkey (Meleagris gallopavo) Isolation and Characterization of IgG, IgM and IgA in Body Fluids, Eggs and Intraocular Tissues", *Poultry Science*, 56, 1847–1851 (1977).

Hadge et al., "Evolution of Low Molecular Weight Immunoglobulins", *Developmental and Comparative Immunology*, 4, 501–513 (1980).

Harlow et al., "Detergents", *Antibodies: A Laboratory Manual*, Cold Spring Harbor Laboratory, 687–689 (1988).

Hassl et al., "Purification of Egg Yolk Immunoglobulins: A Two-Step Procedures Using Hydrophobic Interaction Chromatography and Gel Filtration", *J. of Immuno. Methods*, 110, 225–228 (1988).

Jensenius et al., "Eggs: Conveniently Packaged Antibodies. Methods for Purification of Yolk IgG", *J. of Immuno. Methods*, 46, 63–68 (1981).

Larsson et al., "Chicken Antibodies: Taking Advantage of Evolution—A Review", *Poultry Science*, 72, 1807–1812 (1993).

(List continued on next page.)

Primary Examiner—Christine M. Nucker
Assistant Examiner—Julie Krsek-Staples
Attorney, Agent, or Firm—Merchant, Gould, Smith Edell, Welter & Schmidt

[57] ABSTRACT

The present invention provides a method for purifying high yields of IgG immunoglobulins from an egg yolk by a single phase separation step using a nonionic detergent.

15 Claims, No Drawings

OTHER PUBLICATIONS

Losch et al., "The Chicken Egg, an Antibody Source", *J. Vet. Med.*, 33, 609–619 (1986).

Polson et al., "Isolation of Viral IgY Antibodies from Yolks of Immunized Hens", *Immuno. Communications*, 9, 475–493 (1980).

Polson et al., "Antibodies to Proteins from Yolk of Immunized Hens", *Immuno. Communications*, 9, 495–513 (1980).

Polson et al., "Improvements in the Isolation of IgY from the Yolks of Eggs Laid by Immunized Hens", Marcel Dekker, Inc., 323–327 (1985).

Rose et al., "Immunoglobulins in the Egg, Embryo and Young Chick", *Developmental and Comparative Immunology*, 5, 15–20 and 371–375, (1981).

Shah et al., "Separating Yolk Proteins and Lipids", *Journal of Food Processing and Preservation*, 16, 275 (1992).

Yokoyama et al., "Passive Protective Effect of Chicken Egg Yolk Immunoglobulins Against Experimental Enterotoxigenic Escherichia coli Infection in Neonatal Piglets", *Infection and Immunity*, 60, 998–1007 (1992).

METHOD FOR PURIFYING EGG YOLK IMMUNOGLOBULINS

BACKGROUND OF THE INVENTION

Immunoglobulins play an important role in diagnostic and therapeutic applications. Sera obtained from hyperimmunized mammals has been extensively used to provide immunoglobulins for use in such applications. In certain cases, avian-derived immunoglobulins provide significant advantages over their mammalian counterparts. For example, avian-derived immunoglobulins may provide a higher level of specificity and a reduced amount of undesirable side effects as compared to immunoglobulins derived from mammalian serum.

A useful source of avian IgG immunoglobulins is the yolk of avian eggs. Not only does egg yolk contain high levels of IgG immunoglobulins but it is less labor intensive to collect immunoglobulin-containing eggs from birds than serum from mammals. However, it is necessary to separate the immunoglobulins from other egg yolk constituents such as lipids and lipoproteins to effectively use avian IgG immunoglobulins in assays and therapeutics.

The IgG immunoglobulins in bird egg yolks are hydrophilic and interspersed with non-aqueous components of the yolk. Present methods for separating IgG immunoglobulins from lipids, lipoproteins and other non-aqueous components in egg yolks use multiple treatments with a separating agent. Such methods are time consuming, and often require the use of specialized equipment. For example, in one technique, the aqueous IgG (IgY) immunoglobulins of the egg yolk are separated from the non-aqueous lipids and other components by multiple precipitation extractions using polyethylene glycol (PEG). Polson et al., *Immuno. Communications,* 2:495–514 (1980). The remaining PEG is removed by precipitation of the IgG immunoglobulin fraction with ammonium sulfate or ethanol at subzero temperatures.

In another method, the lipids and lipoproteins of the egg yolk are precipitated using multiple extractions with dextran sulfate and calcium chloride. Jensenius et al., *J. of Immuno. Methods,* 46:63–68 (1981). The IgG immunoglobulins are then precipitated with sodium sulfate, and resolubilized to provide a 70–80% yield of total IgG immunoglobulin concentration in the egg yolk. Another method involves multiple extraction steps using organic solvents at −20° C. Bade et al., *J. of Immuno. Methods,* 72:421–426 (1984). Yet another method utilizes pH adjustment of the egg yolk to separate out the yolk proteins. Jensenius et al., *J. of Immuno. Methods,* 46:63–68 (1981). The yield of IgG immunoglobulins by this method is only about 50–70% of the total IgG in the egg yolk.

Other methods use separation techniques such as hydrophobic interaction chromatography and gel filtration chromatography. Hassl et al., *J. of Immuno. Methods,* 110:225–228 (1988). While such methods purport to provide a relatively pure IgG product, purification of the IgG fraction requires expensive separation equipment, and the overall yield of IgG is relatively low compared to other separation procedures.

Accordingly, an object of the invention is to provide a method for separating and purifying a high percentage of the total IgG immunoglobulin from the yolk of an egg without the need for multiple extraction steps, or expensive separation equipment.

SUMMARY OF THE INVENTION

The present invention is directed to a method for separating IgG immunoglobulins from the yolk of an egg, a composition containing the egg yolk-derived IgG immunoglobulins, and methods of using the IgG immunoglobulin composition in diagnostic assays and therapeutic applications. The method of preparing an IgG immunoglobulin fraction according to the invention, includes the use of a protein non-denaturing, nonionic detergent in a single application to phase separate an aqueous suspension or clarified supernatant of the egg yolk into an aqueous phase containing a major portion of the IgG immunoglobulins of the yolk and a non-aqueous detergent phase containing a major portion of the lipids, lipoproteins and other like constituents. The phase separating conditions used in the method are substantially non-denaturing to the IgG immunoglobulins. The method of the invention provides a high yield of the total IgG immunoglobulins from the egg yolk starting material of about 75–99%, preferably about 85–95%.

In the method of the invention, an egg yolk is combined with an effective amount of an aqueous medium, preferably a buffer solution, to provide an aqueous suspension of the yolk. Preferably, the yolk suspension is clarified, for example, by centrifugation, and the supernatant collected. An effective amount of a nonionic detergent, with octoxynol-8 (TRITON ® X-114) preferred, is added to the yolk suspension or supernatant to form a homogeneous mixture, and the mixture is allowed to separate into an aqueous phase and a non-aqueous detergent phase. The separated aqueous phase contains a major proportion of the IgG immunoglobulins of the egg yolk, while the detergent phase contains a major amount of the lipids, lipoproteins and other hydrophobic substances of the yolk. The aqueous phase may be removed from the non-aqueous detergent phase, for example, by suctioning, decanting, and the like, and further remaining detergent in the aqueous phase may be removed, for example, by a membrane dialysis technique using a physiologically-acceptable dialyzing buffer. The IgG immunoglobulins in the separated aqueous phase may then be used immediately in a diagnostic assay or therapeutic procedure, or may be stored for future use, by known procedures in the art for example, lyophilization or a cryopreservation technique, and the like.

The nonionic detergent used in the method of the invention is substantially protein non-denaturing and capable of providing a two-phase separation of the egg yolk suspension or clarified supernatant when combined therewith. Preferably, the nonionic detergent is capable of causing such phase separation at a temperature which is substantially non-denaturing to the IgG immunoglobulins in the mixture. According to the invention, it is preferred that the temperature at which the detergent causes phase separation of the mixture is from about −25° C. to about 60° C., preferably about −10° C. to about 55° C., preferably about 0°–50° C.

The invention also provides a composition containing the substantially pure IgG immunoglobulin fraction, isolated and purified according to the invention. Preferably, the IgG immunoglobulin fraction is combined with an aqueous, pharmaceutically-acceptable carrier such as water, saline, and the like, and other additives and adjuvants as desired. A composition useful according to the present invention includes an amount of the purified IgG immunoglobulin fraction effective to provide passive immunity in the bird or mammal against an etiological agent of interest.

The invention also provides a method for immunizing a bird or mammal with the IgG immunoglobulin fraction prepared according to the invention, to provide passive immunity protection against a bacterial or viral pathogen, or other etiological agents. The method includes administering to the animal, an effective amount of the IgG immunoglobulin fraction to provide passive immunity against the etiological agent. The antibodies may be administered orally (liquid or bolus), parenterally, (intravenous, intramuscularly, subcutaneously, respiratory aerosolization, metabolizable implant, and other known parenteral routes), or by egg inoculation.

Another therapeutic application in which the IgG immunoglobulin fraction prepared according to the invention may be used includes tumor immuno-diagnosis and/or immunotoxin delivery. For example, antibodies may be made against specific antigens on target cells in the body, such as epitopes on tumor cells. The antibody may be linked to a drug, an isotope, or other labeling system providing for recognition and/or destruction of the targeted cell bearing the antigen to which the specific antibody will bind.

The invention further provides an in vitro method of detecting an etiological agent of interest through the use of the purified IgG immunoglobulin fraction. For example, the yolk-derived IgG immunoglobulin fraction may be combined with a labeling agent such as a radioactive isotope, an enzyme, a dyestuff, a fluorescent group, and the like, or any combination thereof, and used in a diagnostic assay, as for example, an immunofluorescent assay, a radioimmunoassay, and the like, or in an immunoassay such as an immunodiffusion assay, an immunoagglutination assay, and the like.

DETAILED DESCRIPTION OF THE INVENTION

As used herein, the term "cloud point" of a detergent means the point of separation of an aqueous mixture containing the detergent into an aqueous phase and a non-aqueous phase, resulting, at least in part, from the reaction of the detergent with hydrophobic components in the mixture. By the term "substantially pure," it is meant that the IgG immunoglobulins of the egg yolk have been extracted and isolated from their natural association with other substances and elements of the egg yolk to provide a fraction containing essentially IgG, heavy and light chains of IgG and other proteins less than about 50,000 molecular weight.

In the method of the invention, one or more egg yolks which have been separated from the albumen fraction of the egg, and suspended in an aqueous medium are treated with a single application of a phase-separating nonionic detergent to separate and purify the IgG immunoglobulins from the egg yolk.

Using known techniques, an egg-laying female bird such as a turkey, chicken, duck, goose, pigeon, pheasant, quail, and other like birds, or an egg-laying reptile such as a snake, turtle, and the like, may be immunized with an antigen to stimulate production of an IgG immunoglobulin of interest. The antigen may be a pathogenic gram negative or gram positive bacteria, or subunit thereof (e.g., outer membrane protein), a toxin, an allergen, a hormone, or any other material capable of stimulating immunoglobulin production.

Examples of gram negative bacteria which may serve as antigens for immunizing the animal include *Escherichia coli*, Salmonella spp., *Bordetella avium*, Pasteurella spp., Hemophilus spp., Pseudomonas spp., Neisseriaceae spp., Shigella spp., Vibrio spp., and the like. Examples of gram positive organisms which may be antigens include Staphylococcus spp., Streptococcus spp., Erysipelothrix spp., Clostridium spp., and the like. Other organisms which may serve as antigens include, for example spirochetes such as Borrelia spp., and the like; fungi such as Aspergillus spp., Fusarium spp., Trichophyton spp., Candida spp., and the like; protozoa including Treponema spp., Toxoplasm spp., Giardia spp., Cryptococcus spp., Coccidia spp., and the like; nematodes including Ascaris spp., Trichinella spp., and the like; Platyhelminthes such as flukes, tapeworms, and the like; and RNA and DNA viruses.

Toxins which may serve as antigens include venoms from reptilia such as snakes, lizards, and the like; and venoms from arachnida such as spiders, scorpions, and the like. Examples of other toxins which serve as suitable antigens include bacterial endotoxins and/or exotoxins such as those produced by *Escherichia coli;* enterotoxins including heat labile enterotoxin (LT) and heat stable enterotoxin (ST); and verotoxin (VT). Also included are diphtheria and tetanus toxin, and other toxins including algal and fungal toxins, and the like.

Allergens may also serve as antigens for producing antibodies according to the method of the invention. Examples of allergens useful in the present method include pollens, mold spores, dust, and the like.

Hormones are also useful as antigens for antibody production in the method of the invention. These include testosterone, prolactin, estrogen progesterone, follicle stimulating hormone (FSH), luteinizing hormone (LH), prostaglandins and the like. Also, major histocompatibility complex antigens may serve to stimulate IgG immunoglobulins such as Class I, II and III antigens. In addition, B and T cell markers, lymphokines such as interferon, interleukins, tumor necrosis factor (TNF), prostaglandins, and the like, may also be used as antigens.

Such immunization will stimulate the female animal to produce eggs containing a high level of the IgG immunoglobulin of interest. The IgG immunoglobulins in the resulting eggs may then be separated and purified according to the method of the invention to provide a purified IgG immunoglobulin fraction containing high levels of the immunoglobulin of interest. It is understood, according to the invention, that IgG immunoglobulins may be isolated from egg yolks derived from an animal which has not been hyperimmunized to produce a high level of IgG immunoglobulins.

According to the invention, the source of egg yolk may be derived from a single species or a combination of different species. The albumen fraction, located external to the yolk within the shell of an egg, generally contains a major amount of IgM and IgA immunoglobulins, and a minor amount of IgG immunoglobulins, and the egg yolk contains a major amount of IgG immunoglobulins. The yolk portion may be separated from the albumen of the egg by known techniques including, for example, breaking the egg in half and separating the albumen from the yolk by passing the yolk from one half shell to the other half shell, by means of an egg yolk separating device which has a recessed surface portion to receive the egg such that the albumen drops off the side edges and the yolk remains in the recessed portion (Egg Separator), such as that commercially available from EKCO Housewares, Franklin Park, Ill., by means of an automatic egg breaking and separating machine such as that commercially available from Sanova Engineering, Salt Lake City, Utah, and other like separation methods.

It is preferred that any albumen remaining on the yolk is removed, for example, by gently applying a stream of water onto the yolk, by gently rolling the yolk on a paper towel, and the like. If desired, the vitelline membrane encasing the yolk may be allowed to separate out at centrifugation or can be removed manually.

The separated yolk fraction is then combined with an aqueous medium such as water, an aqueous buffer, and the like, to form a suspension of the egg yolk. Preferably, the aqueous medium is a physiologically-acceptable buffer solution formulated to maintain the egg yolk suspension at about pH 5.5–9.5, preferably about pH 6.0–9.0, preferably about pH 6.5–8.5. Buffers suitable for use according to the invention include, for example, phosphate-buffered saline (PBS), Tris (hydroxymethyl) aminomethane (Tris), tris-buffered saline (TBS), N-2-hydroxyethylpiperazine-N'-2-ethanesulfonic acid (HEPES), 3-(N-morpholino)propanesulfonic acid (MOPS), and the like. Preferably, the egg yolk fraction is combined with the aqueous medium in a ratio of egg yolk:aqueous media of about 1:1 to about 1:40, preferably about 1:10 to about 1:30 v/v, preferably about 1:15 to about 1:25, preferably about 1:20.

It is preferred that insoluble materials such as lipoproteins, phospholipids, sterols, and the like, are removed from the aqueous yolk suspension. For example, the yolk suspension may be centrifuged at about 20,000–30,000 X g. The clarified supernatant which contains the IgG immunoglobulins may then be separated from the precipitant or sediment, for example, by decanting, suctioning, and other like methods. Optionally, the supernatant may be recentrifuged one or more times to further clarify the supernatant fraction as desired.

The clarified yolk supernatant is then treated with a nonionic detergent to cause a phase separation of the suspension or supernatant into an aqueous phase and non-aqueous detergent phase. The nonionic detergent is substantially non-denaturing to the IgG immunoglobulin proteins of the suspension or supernatant. The detergent is also capable of forming a mixture with the aqueous yolk suspension or clarified supernatant, and then separating the mixture into two phases, an aqueous phase and a non-aqueous detergent phase. Preferably, the nonionic detergent is capable of combining with a major portion of the lipids, lipoproteins and other hydrophobic constituents of the egg yolk to form the non-aqueous detergent phase. It is further understood that multiple detergents sequentially mixed with the egg yolk suspension or clarified supernatant, may be utilized to enhance IgG immunoglobulin extraction.

Preferably, the nonionic detergent is capable of causing phase separation of the egg yolk suspension or clarified supernatant under conditions such as temperature, pH and salt concentration which are substantially protein non-denaturing, particularly non-denaturing to the IgG immunoglobulins. As used herein, the term "protein non-denaturing" means that the protein substantially maintains its structure and/or functional characteristics.

Preferably, the nonionic detergent is capable of causing separation of a detergent mixture containing the yolk suspension or clarified supernatant at a temperature of about −25° C. to about 60° C., preferably about 10°–55° C., preferably 0°–50° C., a pH of about 5.5–9.5, preferably about pH 6.0–9.0, preferably about pH 6.5–8.5.

Nonionic detergents useful according to the invention include, for example, octoxynol-8 (TRITON® X-114), and other like polyoxyethylene ethers available commercially in the TRITON® X series (Union Carbide) or IgePal™ CA series (GAF). A highly preferred nonionic detergent according to the invention, is TRITON® X-114 or TRITON® X-100, added to the yolk suspension or supernatant as an about 0.5%–13% solution, preferably an about 2–12% solution.

Preferably, the nonionic detergent is combined with a compatible, physiologically-acceptable aqueous medium such as water, a buffer solution, and the like. Suitable buffers for combining with the detergent include, for example, Tris(hydroxymethyl)aminomethane (Tris), tris-buffered saline (TBS), phosphate-buffered saline (PBS), N-2-hydroxyethylpiperazine-N'-2-ethanesulfonic acid (HEPES), 3-(N-morpholino)propanesulfonic acid (MOPS), and the like. Preferably, the detergent is combined with the aqueous medium to provide a mixture containing about 100 to 500,000 ppm detergent. For example, for Triton® X-114, a preferred mixture contains the detergent at a concentration of about 1000 to 100,000 ppm, preferably about 5000 to 80,000 ppm, preferably about 10,000 to 70,000 ppm.

The aqueous yolk suspension or, preferably, the clarified supernatant, is combined with an effective amount of the nonionic detergent to cause phase separation of the resulting mixture within about 5 minutes to about 2 hours, preferably about 15–60 minutes, preferably about 30–45 minutes, with a major portion of the lipids, lipoproteins and other hydrophobic constituents of the egg yolk combining with the detergent in a non-aqueous phase separate from the aqueous phase containing a major portion of the IgG immunoglobulins of the yolk. The amount of detergent combined with the yolk suspension or supernatant will vary according to the concentration of the detergent, the concentration of the yolk in the suspension or supernatant, and the salt concentration to provide substantially complete separation of the IgG immunoglobulins into the aqueous phase, and apart from other non-aqueous substances of the yolk. Suitable concentrations of detergent are about 1–12% w/v. In a preferred method according to the invention, Triton® X-100 or Triton® X-114 is added to the clarified egg yolk supernatant until the desired w/v percentage concentration of detergent is obtained. For example, to cause phase separation of an about 250–300 ml clarified yolk supernatant, about 6–12% w/v of octoxynol-8 (TRITON® X-114) may be added to the supernatant.

It is preferred that the detergent mixture is gently agitated to provide a homogenous mixture of the detergent and the yolk suspension or supernatant, preferably for about 10 minutes to about 3 hours, preferably about 15 minutes to about 2 hours, preferably about 30–60 minutes. It is also preferred that the mixing speed used is effective to thoroughly mix the detergent with the suspension or supernatant, yet avoid denaturing the IgG immunoglobulins. Preferably, the mixing speed is about 50–150 rpm, preferably about 60–100 rpm, preferably about 70–85 rpm. It is also preferred that the temperature of the detergent mixture is maintained at about −25° C. to about 60° C., preferably about −10°-55° C., preferably about 0-50° C., and the pH is maintained at about pH 5.5-9.5, preferably about pH 6.0-9.0, preferably about pH 6.5-8.5.

The detergent mixture is then allowed to separate into a relatively clear aqueous phase and a non-aqueous, relatively viscous, detergent phase. The mixture is maintained at a temperature of about −25° C. to about 60° C., preferably about −10° C. to about 55° C., preferably about 10°-50° C., during the phase separation step. According to the invention, it is preferred that about 90-95% of the detergent phase falls out of the mixture within about 30-60 minutes at a temperature of about 30°-50° C. To enhance separation of the two phases, the mixture may be centrifuged at a low speed, preferably about 500-1,000 rpm for about 10-30 minutes.

The phase separation by the nonionic detergent may also be enhanced and/or activated, for example, by raising or lowering the temperature, pH and/or salt concentration of the detergent mixture. For example, the temperature of the detergent mixture may be raised up to about 40°-60° C., preferably up to about 45°-50° C., or lowered down to about 0° C. to about −25° C., preferably down to about −4° C. to about 5° C. The pH of the detergent mixture may be adjusted to effect phase separation by adding an effective amount of acid and/or base at about 0.01 to 0.1 normality. In addition, the salt concentration of the mixture may be altered, higher or lower, to enhance phase separation by adding an effective amount of potassium chloride or sodium chloride, as desired.

After the mixture is separated into the two phases, the aqueous layer is removed from the non-aqueous detergent layer by known techniques, for example, by decanting, suction pipetting, and the like. According to the invention, the aqueous layer contains a major portion of the total IgG immunoglobulins of the egg yolk starting material, IgG extraction from the aqueous phase is about 51-99%, preferably about 70-97%, preferably about 80-95%. The detergent layer contains a major portion of the total lipids and lipoproteins of the egg yolk starting material, or about 51-99%, preferably about 70-97%, preferably about 80-95%.

Residual nonionic detergent remaining in the aqueous phase may optionally be removed by known methods, for example, by membrane dialysis, gel filtration, ion exchange chromatography, affinity chromatography, and other like methods for separating molecules of different molecular weight and/or polarity. For example, the aqueous phase may be treated by gel filtration using a gel made of dextran and acrylamide such as SEPHACRYL S-300®, available commercially from Pharmacia, Piscataway, N.J.

Preferably, residual nonionic detergent is removed from the aqueous phase by membrane dialysis. For example, the aqueous phase may be diluted with a physiologically-compatible buffer such as phosphate buffered saline (PBS), and placed into a dialysis membrane in the form of a tube or bag, and submerged in a compatible physiological dialysis buffer, as for example, a physiological saline solution (0.85%), a 5% glucose in physiological saline solution (0.85%), Tris(hydroxymethyl)aminomethane (Tris), tris-buffered saline (TBS), phosphate-buffered saline (PBS), N-2-hydroxyethylpiperazine-N'-2-ethanesulfonic acid (HEPES), 3-(N-morpholino)propanesulfonic acid (MOPS), and the like. Detergent molecules in the aqueous phase within the dialysis tube will then pass through the dialysis membrane into the dialysant outside the tube. Preferably, the pore size of the dialysis membrane is effective to retain IgG immunoglobulins having a molecular weight of about 150,000-180,000 daltons within the bag, and allow passage of detergent molecules having a molecular weight of about 1-145,000 daltons, preferably about 1,000-125,000 daltons, preferably about 5,000-100,000, out of the bag into the dialysis solvent. Dialysis membranes suitable for use in the present method include, for example, SPECTRA POR® MWCO 3500, SPECTRA/POR #7® MWCO 50,000, and the like, available commercially from Spectrum Medical Industries Inc., Los Angeles, Calif.

The dialysis treatment of the aqueous phase, or other like treatment to remove the residual detergent, results in a substantially pure aqueous IgG immunoglobulin fraction comprising a major amount of the IgG immunoglobulins of the yolk starting material, or about 51-99%, preferably about 60-95%, preferably about 70-90%.

A composition according to the invention contains the resulting substantially pure IgG immunoglobulin fraction in combination with a physiologically-acceptable carrier, and other additives and adjuvants as desired. Suitable carriers include, for example, water, saline, phosphate buffered saline (PBS), Tris(hydroxymethyl)aminomethane (Tris), tris-buffered saline (TBS), N-2-hydroxyethylpiperazine-N'-2-ethanesulfonic acid (HEPES), 3-(N-morpholino) propanesulfonic acid (MOPS), and the like. Additive agents which may be included in the composition include, for example, an effective amount of a preserving agent such as bacteriostats, fungistats, and the like. In addition, to prevent precipitation of the globulin, an effective amount of glucose (5%), and the like, may be added.

The purified IgG immunoglobulin fraction may be used immediately or stored for future use. For example, the IgG immunoglobulin fraction may be cryopreserved by combining the fraction with a compatible isotonic solution, and stored at a temperature about −45° C. to about 4° C., preferably about −30° C. to about −10° C. To prevent precipitation of the IgG immunoglobulins upon thawing of a cryopreserved solution, a compatible protein precipitation-preventing agent may be included in the composition, as for example, an aqueous solution of about 5% glucose w/v in physiological saline (0.85%), and the like.

The invention also provides a method for immunizing domestic fowl, livestock, horses, companion animals and humans with the purified IgG immunoglobulin fraction prepared according to the invention to provide passive immunity protection against various etiological agents, including, for example, bacteria, viruses, fungi, protozoa, nematodes, platyhelminthes, and the like. In addition, the method of the invention provides for passive immunization against allergens, toxins, venoms, hormones, or any other immunogen capable of eliciting an immune response. The method includes administering to the animal, an effective therapeutic amount of the substantially pure IgG immunoglobulin fraction to provide passive immunity against the etiological agent. Preferably, the animal is administered the purified IgG immunoglobulin fraction combined with a pharmaceutically-or physiologically-acceptable carrier such as water, saline, and the like.

The composition may be administered to the animal orally or parenterally, by suppository, by injection, by aerosolization or by other suitable means and techniques known in the art. For example, the composition may be formulated with conventional pharmaceutically- or physiologically-acceptable parenteral vehicles for administration by injection. These vehicles comprise substances that are essentially nontoxic and nontherapeutic such as water, saline, dextrose solution, Hank's Solution, and the like. It is to be understood that immunoglobulin formulations may also include small amounts of diluents such as buffers and preservatives to maintain isotonicity, physiological pH and stability. The composition may be administered to an animal on a periodic or continuous basis.

Preferably, the purified IgG immunoglobulin fraction is administered to the animal orally, parenterally, (intravenously, intramuscularly, subcutaneously, respiratory aerosolization), by metabolizable implant, and the like. In such application, the IgG immunoglobulin fraction is a constituent in a suitable liquid media such as water and the like, or a feed in an appropriate dry format, or a tablet or other oral form understood by those skilled in the art. As described hereinabove, the oral composition can include suitable compatible diluents. The specific IgG immunoglobulin of interest is contained in the purified immunoglobulin fraction provided to a patient. In such form, the immunoglobulin concentration provided to the animal is about 0.25-20 grams per day. For example, about 0.5-1 grams of immunoglobulin could be given to a animal at 3 to 4 times per day. The doses of the immunoglobulin formulation to be administered will depend upon the type of animal, size, and the like.

In a preferred method according to the invention, a therapeutically effective amount of the purified immunoglobulin fraction of IgG can be given passively to the developing turkey or chicken embryo during the incubation period. The immunoglobulins can be administered in ova into the albumin which is swallowed by the developing chick, or into the yolk sac where it is absorbed, to provide systemic and intestinal passive protection. The method of in ova injection by modular injection system is described, for example, in U.S. Pat. No. 5,136,979 the disclosure of which is incorporated by reference herein.

The IgG immunoglobulin fraction of the present invention may also be used for in vitro detection of an etiological agent, for example, a pathogenic organism such as *Escherichia coli, Salmonella enterititis, Bordetella avium, Pasteurella multocida*, and other bacterial organisms; a hormone such as estrogen, progesterone and the like; a major histocompatibility complex antigen, and the like; in a body sample such as a fluid, tissue, cell extract, and the like, that is obtained from the human or animal for testing. A method for in vitro detection of an etiological agent in a body sample would include combining the body sample with an effective amount of the purified IgG immunoglobulin fraction prepared according to the method of the invention, with the IgG immunoglobulin in the fraction being labeled. The label may be any labeling group that may be suitably bound to the IgG immunoglobulin or second immunoglobulin or antibody, and which will allow for the reaction with the antigen of interest in the sample. The label may be, for example, a radioactive group such as $^{124}I$, $^{14}C$, $^{3}H$, and the like; an enzymatic label such as horseradish peroxidase, a catalase, a glucose oxidase, and the like; a fluorescent label such as rhodamine, fluorescein, and the like; a fluorescent label such as rhodamine, fluorescein and the like; an immuno-electron microscopy conjugate such as a gold conjugate and the like; and an immuno diagnostic label for protein blotting, and the like, using alkaline phosphates, biotin, and the like; and other like labeling agents. The body sample is combined with the labeled IgG immunoglobulin for a time effective to allow binding of the labeled IgG immunoglobulin with the body sample evidencing the presence of the etiological agent. The presence of the labelled IgG immunoglobulin bound to the body sample is then detected, for example, by techniques known in the art, including color changes, autoradiography, positron emission tomography, nuclear magnetic resonance imaging, a gamma counter, a scintillation counter, and the like. The detection method may also include quantifying, by known techniques, the amount of labeled antibody that is bound to the sample.

An example of an in vitro method of detecting an etiological agent in a body sample is by immobilizing the IgG immunoglobulins of the purified fraction on a solid phase support, as for example, immunomagnetic beads, a resin test plate such as polyvinylchloride, polystyrene and the like, or a nitrocellulose carrier and the like, in an amount effective to bind with a fluid, tissue, or other body sample that evidences the presence of the antigen of interest, such as that associated with *Borrelia burgdorferi* (Lymes Disease), *Mycobacterium tuberculosis* (TB), Histoplasmosis spp., or any other etiological agent expressing antigens capable of eliciting an immune response. An example of a useful composition for detecting an antigenic etiological agent in a sample in vitro is one that includes about 1 to 100 $\mu$g of the IgG immunoglobulin per $2 \times 10^8$ immunomagnetic beads.

In another example of detecting an etiological agent in a body sample in vitro, the purified IgG immunoglobulin fraction may be combined with the sample, and after a suitable reaction time, the IgG immunoglobulin that is bound to the sample is detected by a suitable method known in the art. In one example of such an assay, the purified IgG immunoglobulins of the purified fraction may be labeled and immobilized onto a solid phase carrier according to techniques known in the art, and then reacted with the antigen of interest in the sample, or fragment thereof that includes the epitopal-binding site(s) for the IgG immunoglobulin, to form a complex between the labeled IgG immunoglobulin and the antigen. The carrier with the bound IgG immunoglobulin/antigen complex would then be washed to remove unbound materials, and the labeled IgG immunoglobulin in the complex detected by conventional methods known in the art. As another example, the sample may be immobilized onto a solid phase carrier according to conventional methods in the art, and reacted with the labeled IgG immunoglobulin. The carrier with the bound complex would then be washed to remove unbound material and the labeled IgG immunoglobulin in the complex would be detected.

EXAMPLE 1

IgG Immunoglobulin Purification Using 6% Triton X-114

Twenty eggs were collected from twenty female chickens, and the egg yolks were separated from the albumen fraction of the egg by cracking the egg into an EKCO ® Egg Separator (EKCO Housewares, Franklin Park, IL). This application holds the yolk stationary while allowing for the separation of albumen. The yolk, while still in the applicator is rinsed in a stream of distilled water to remove any excess albumen that may cling to the yolk. The washed egg yolks (100 grams; 4 egg yolks) were then combined together in a beaker, combined with an equal amount (100 ml) of tris-buffered saline (TBS; i.e., Tris(hydroxymethyl) aminomethane) (pH 7.4), and mixed thoroughly using a magnetic stirrer at 100–200 rpm for 10 minutes to form a suspension of the egg yolks in the buffer.

The egg yolk/buffer suspension (20 grams) was diluted 1:10 in tris-buffered saline TBS buffer (pH 7.4), mixed thoroughly using a magnetic stirrer at 200 rpm for 5 minutes, and centrifuged at 22095 X g for 25 minutes in a Beckman J2-21M centrifuge (Beckman Instruments, Palo Alto, Calif.), to remove insoluble material. The supernatant was collected by suctioning the supernatant, and the insoluble material was discarded. The supernatant was recentrifuged at 22095 X g for 25 minutes to further clarify the supernatant. The clarified supernatant (270 ml) was combined with 180ml of 6% Triton X-114 ® in tris-buffered saline (TBS) (pH 7.4). The buffer mixture was held at 4° C. in a 500 ml screw capped erlenmeyer flask while continuous stirring at 200 rpm, for 30 minutes.

The mixture was allowed to warm to 37° C. by maintaining the mixture at a stationary condition. As the mixture warmed, phase separation occurred. At the same time, the water phase (containing the IgG immunoglobulins) formed a layer over the TRITON ® detergent layer. The water phase was relatively clear while the non-aqueous TRITON ® X114 detergent phase was viscous and appeared yellowish in color. The upper aqueous layer was collected by suction into a reservoir vessel.

The aqueous phase was then clarified by centrifuging at 15344 X g for 10 minutes at 25° C. After the centrifugation, glucose, at 5% w/v concentration was added to the aqueous solution (17.5 grams) was added to 350 ml aqueous phase supernatant to prevent precipitation of the immunoglobulins from solution. The supernatant was then dialyzed against a physiological saline solution (0.85%) containing 5% glucose (Sigma Chemical Co., St. Louis, Mo.) for 48 hours at 4° C., to remove residual contaminating TRITON ® detergent in the aqueous IgG immunoglobulin fraction.

The process yielded an aqueous solution (350 ml) containing about 85% of the total IgG immunoglobulins of the egg yolk starting material.

EXAMPLE 2

Immunization Procedure for Stimulation of Specific Antibody Production

Eighty, 12-week old, shaver white chickens were equally divided among ten groups. Chickens were vaccinated with the following antigens: outer membrane proteins of *Escherichia coli, Bordetella avium, Staphylococcus areus;* pili antigens of *Escherichia coli* (K88, K99, 987P and F41); New Castle Disease Virus (NDV) and hemorrhagic enteritis. The birds were given three additional boosters at fourteen day intervals.

One week after the last booster injection, eggs were collected from all groups of birds over eighteen days. On the eighteenth day all groups were again vaccinated with the appropriate antigen and eggs were again collected. This procedure was repeated for the duration of the experiment.

Yolks were harvested and processed as described in Example 1. The IgG was collected from each group and stored at −95° C. The affinity of the IgG for each group was determined using a standardized Enzyme Linked Immunoadsorbent Assay (ELISA) for each group of antigens.

The invention has been described with reference to various specific and preferred embodiments and techniques. These examples are not meant to limit the scope of the invention that has been set forth in the foregoing description. It should be understood that many variations and modifications may be made while remaining within the spirit and scope of the invention. The disclosures of the references cited in the disclosure are incorporated by reference herein.

What is claimed is:

1. A method for separating an IgG immunoglobulin from a yolk of an egg, comprising:
   (a) combining the egg yolk with an effective amount of an aqueous medium to provide an aqueous suspension of the egg yolk;
   (b) combining the aqueous egg yolk suspension with a nonionic detergent at a temperature of about −25° C.–60° C. and a pH of about 5.5–9.5 to form a mixture; the amount of the nonionic detergent effective to provide phase separation of the egg yolk phase; the nonionic detergent being substantially non-denaturing to the IgG immunoglobulin;
   (c) allowing the mixture to separate into an aqueous phase and a non-aqueous detergent phase wherein the aqueous phase contains a major portion of the IgG immunoglobulins of the egg yolk; and
   (d) separating the aqueous phase from the non-aqueous detergent phase, to provide an aqueous, substantially pure IgG immunoglobulin fraction.

2. The method according to claim 1, wherein the egg yolk is combined with the physiological buffer in a ratio of about 1:5 to about 1:30 v/v.

3. The method according to claim 1, wherein the nonionic detergent in step (b) is an ethoxylated alkyl phenol.

4. The method according to claim 3, wherein the nonionic detergent is an octoxynol.

5. The method according to claim 1, wherein step (b) comprises combining the detergent with the egg yolk suspension to obtain a mixture containing about 1–12% w/v detergent to egg yolk suspsension.

6. The method according to claim 1, wherein the phase separation of the mixture in step (c) is activated by raising or lowering the temperature of the mixture, by increasing the salt concentration of the mixture, by raising or lowering the pH of the mixture, or a combination thereof.

7. The method according to claim 4, wherein the phase separation of the mixture in step (c) is activated by raising, lowering, or sequentially raising and lowering the temperature of the mixture, up to about 20°–60° C. and down to about 10° to about −25° C.

8. The method according to claim 1, wherein the aqueous phase in step (d) contains about 51–99% of the total IgG immunoglobulins in the egg yolk.

9. The method according to claim 1, wherein step (d) comprises removing the aqueous phase by suctioning or decanting.

10. The method according to claim 1, wherein step (d) comprises removing residual nonionic detergent in the separated aqueous phase.

11. The method according to claim 10, wherein the residual nonionic detergent is removed by membrane dialysis of the aqueous phase against a physiological dialyzing solvent.

12. The method according to claim 11, wherein the membrane dialysis includes using a dialysis membrane having a pore size effective to allow passage of molecules of less than about 100,000 daltons and retention of molecules of greater than about 100,000 daltons.

13. The method according to claim 12, wherein the pore size of the membrane is effective to allow passage of molecules of about 5,000 to about 100,000 daltons.

14. The method according to claim 1, wherein the egg yolk is derived from an egg from a chicken, turkey, duck, goose, pheasant, pigeon, quail, or any combination thereof.

15. The method according to claim 14, wherein the egg yolk is derived from an egg from a chicken, turkey, or any combination thereof.

* * * * *

UNITED STATES PATENT AND TRADEMARK OFFICE
CERTIFICATE OF CORRECTION

PATENT NO. : 5,420,253

DATED : May 30, 1995

INVENTOR(S) : Emery et al.

It is certified that error appears in the above-identified patent and that said Letters Patent is hereby corrected as shown below:

At Col. 1, line 38, delete "2:495" and insert therefor --9:495--.

Signed and Sealed this

Fifth Day of December, 1995

Attest:

BRUCE LEHMAN

*Attesting Officer*   Commissioner of Patents and Trademarks